United States Patent [19]

Churinetz et al.

[11] Patent Number: 5,312,333
[45] Date of Patent: May 17, 1994

[54] ENDOSCOPIC MATERIAL DELIVERY DEVICE

[75] Inventors: Robert Churinetz, West Haven; Jeffrey S. White, Ridgefield, both of Conn.

[73] Assignee: United States Surgical Corporation, Norwalk, Conn.

[21] Appl. No.: 863,195

[22] Filed: Apr. 3, 1992

[51] Int. Cl.⁵ .............................................. A61M 5/00
[52] U.S. Cl. ...................................... 604/57; 604/58; 604/140; 604/148
[58] Field of Search ..................... 604/57-61, 604/64, 140, 141, 143, 145-148

[56] References Cited

U.S. PATENT DOCUMENTS

| | | | |
|---|---|---|---|
| 1,642,950 | 9/1927 | Haas | 604/58 |
| 2,554,352 | 5/1951 | Ward et al. | 604/148 |
| 2,623,519 | 12/1952 | Cohen | 604/141 |
| 2,647,512 | 8/1953 | Johnson | 604/64 |
| 3,088,207 | 5/1963 | Borsuk | 604/61 |
| 3,561,433 | 2/1971 | Kovach . | |
| 3,744,493 | 7/1973 | Booher et al. | 604/60 |
| 3,934,584 | 1/1976 | Corio | 604/59 |
| 4,154,239 | 5/1979 | Turley | 604/61 |
| 4,237,871 | 12/1980 | Bonnet . | |
| 4,349,028 | 9/1982 | Green . | |
| 4,426,024 | 1/1984 | Hogan et al. | 604/141 |
| 4,522,621 | 6/1985 | Cassou | 604/140 |
| 4,597,753 | 7/1986 | Turley | 604/61 |
| 4,790,819 | 12/1988 | Li et al. | 604/59 |
| 4,944,726 | 7/1990 | Hilal et al. | 604/143 |
| 4,977,900 | 12/1990 | Fehling et al. . | |
| 5,015,233 | 5/1991 | McGough et al. | 604/146 |
| 5,024,656 | 6/1991 | Gasaway et al. | 604/141 |
| 5,046,486 | 9/1991 | Grulke et al. . | |
| 5,125,836 | 6/1992 | Dragan et al. . | |
| 5,129,882 | 7/1992 | Weldon et al. | 604/96 |
| 5,133,701 | 7/1992 | Han | 604/289 |
| 5,200,170 | 4/1993 | McDow | 604/289 |
| 5,221,259 | 6/1993 | Weldon et al. . | |
| 5,222,939 | 6/1993 | Tiefenbrun et al. . | |
| 5,224,931 | 7/1993 | Kumar . | |

FOREIGN PATENT DOCUMENTS

| | | | |
|---|---|---|---|
| 81392 | 6/1983 | European Pat. Off. | 604/61 |
| 0436353A1 | 10/1991 | European Pat. Off. . | |
| 3909999 | 3/1989 | Fed. Rep. of Germany . | |
| 84117 | 8/1935 | Switzerland | 604/148 |
| 26666 | of 1903 | United Kingdom | 604/289 |

OTHER PUBLICATIONS

"Toy-Smoot Laparoscopic Hernioplasty", Toy et al., Surgical Laparoscopy & Endoscopy, vol. 1, No. 3, pp. 151-155, 1991.

"Use of an Oxidized, Regenerated Cellulose Absorbable Adhesion Barrier at Laparoscopy", Ricardo Azziz, M.D. et al., Journal of Reproduction Medicine, vol. 36, No. 7, Jul. 1991.

"Laparoscopic Application of Interceed (TC7) in the Pig", Michael P. Diamond et al. Journal of Gynecologic Surgery, vol. 5, No. 2, 1989.

"Cellulose Barrier cuts Adhesion Risk After Infertility Procedures", OB/GYN News, May 1-14, 1990.

Linksy et al., Journal of Reproductive Medicine, vol. 32, No. 1, Jan. 1987.

Diamond et al, Microsurgery 8: 198-200, 1987.

Fertility and Sterility, vol. 51, No. 6, Jun. 1989.

Intercede Product Literature, 1989.

Primary Examiner—Ralph Lewis

[57] ABSTRACT

A device for delivering a quantity of material endoscopically to an intended site of application within a body through an incision or entrance wound includes a handle portion with movable trigger means, and an endoscopic portion. A reservoir or cartridge containing material for delivery may be disposed in the handle or endoscopic portion of the delivery device. In operation, the trigger means may be operated in such a manner so as to cause a discharge of a metered quantity of material from the proximal end of the endoscopic tube.

18 Claims, 3 Drawing Sheets

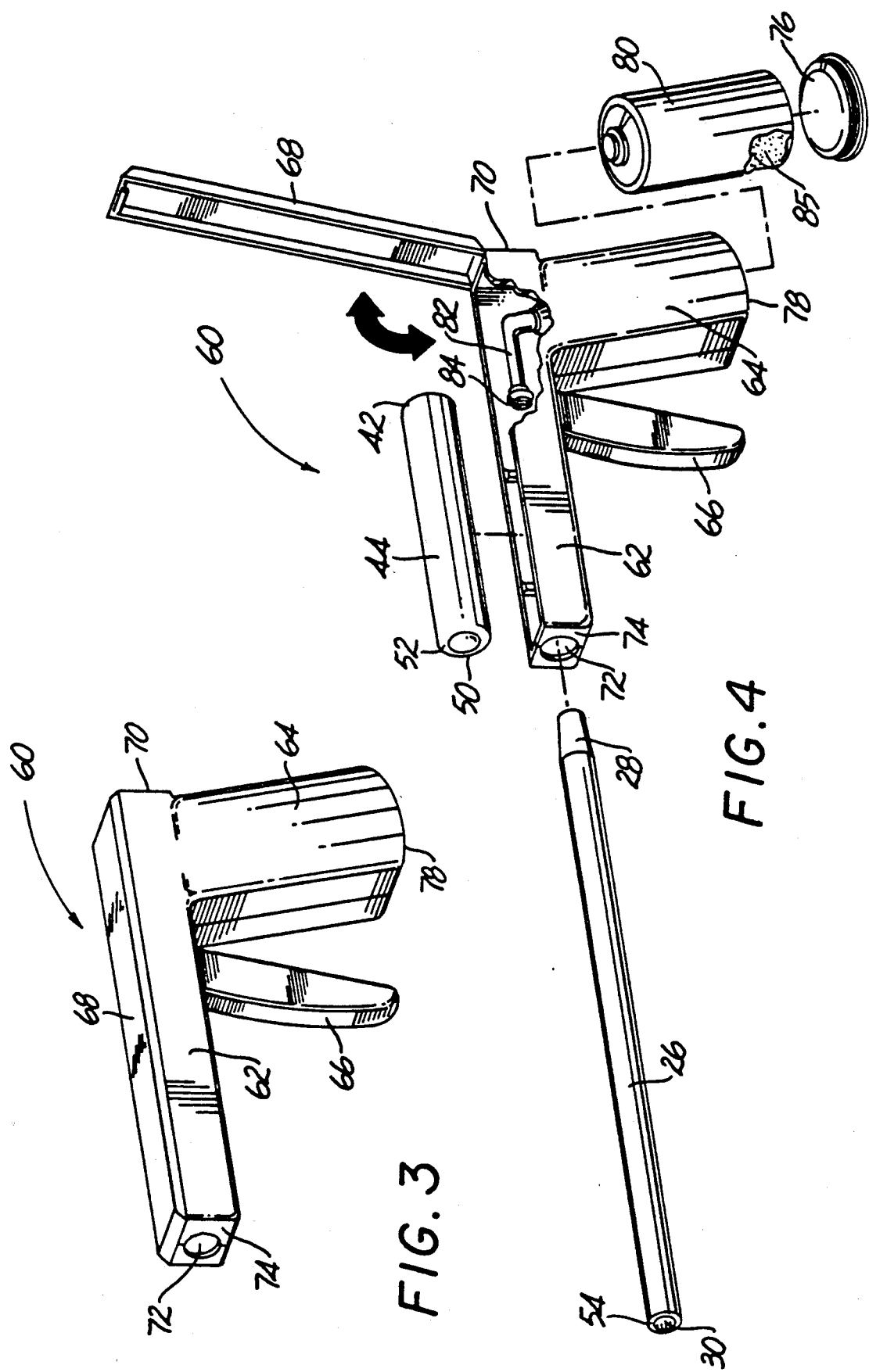

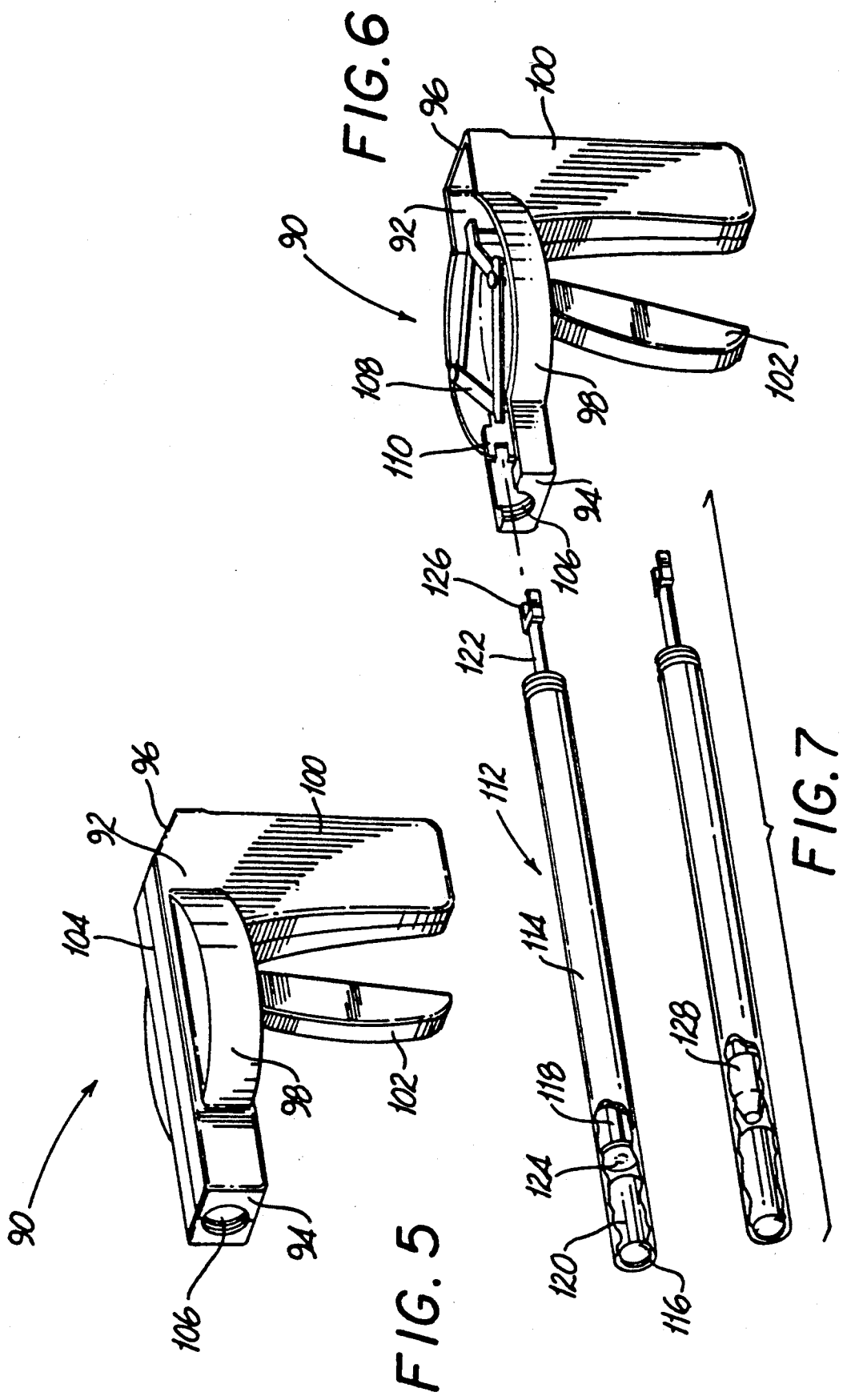

5,312,333

ENDOSCOPIC MATERIAL DELIVERY DEVICE

BACKGROUND OF THE INVENTION

1. Field of the Invention

This invention relates to a device for delivering material to a remote location and more particularly, to an instrument for endoscopic delivery of a quantity of medicament or material to a remote location within the body.

2. Description of the Related Art

In laparoscopic procedures, surgery is performed through a small incision or entrance wound in the skin with the abdominal cavity expanded by gas insufflation. Laparoscopic procedures generally require that any instrumentation inserted into the body be sealed so that gases do not enter or exit the body through the incision. Further, laparoscopic procedures often require the surgeon to operate on organs or tissues which are far removed from the incision, thereby requiring that any instruments to be used in such procedures be both elongated and narrow.

In open surgery, hemostasis is achieved by using agents such as collagen and cellulose in either a preformed pad or a loose powdered form. These hemostatic agents are applied to sites of hemorrhage or bleeding intraoperatively and, due to their thromboplastic nature, cause cessation or reduction of bleeding. A hemostatic collagen paste which may be used in this manner is disclosed in U.S. Pat. No. 4,891,359 to Saferstein et al. These materials are easily applied by hand during open surgery because the site of intended application is readily accessible.

The use of hemostatic agents and other medicaments in laparoscopic surgery poses unique problems due to the limited access to the site of application and the difficulty of passing material to the site via a cannula or trocar. During laparoscopic procedures, materials, such as adhesion barriers, have been delivered to an intended site of application by grasping the material with a micrograsper or other similar instrument, and extending the instrument through a cannula placed in an incision or entrance wound. However, it would be difficult to repetitively deliver a metered quantity of fluid or powdered material in such a manner. Once the material has been introduced into the abdominal cavity, post-insertion manipulation of the material is also extremely difficult.

In addition, because of the difficulty and expense of cleaning and sterilizing surgical instruments between uses, there is an increasing demand for instruments which are disposable after use in a single surgical procedure rather than permanent and reusable. Additionally, instrumentation which requires the use of external power supplies is less efficient for clinical applications.

SUMMARY OF THE INVENTION

An endoscopic device is disclosed for delivering a quantity of material to an organ or tissue area within a body. The device includes an endoscopic portion having a passageway formed therein, material containment means communicating with said passageway and actuating means for causing the delivery of a quantity of material from the material containment means. The device may further include separate propellant containment means for dispensing powder or particulate medicaments. Alternatively, the material containment means may also contain a propellant. The material containment means may comprise a reservoir integrally formed in the endoscopic portion or in a handle portion. Preferably, the containment means comprises a removable cartridge.

The actuating means may be pivotal and may include a trigger. A plunger means operatively connected to the trigger may also be included for advancing distally against the containment means in such a manner as to cause a predetermined quantity of medicament to be expelled from the containment means such as, for example by a propellant.

In another aspect the present invention, the material for delivery to the intended site of application is disposed in the axial passageway of the endoscopic portion of the delivery device. In this instance, the material may comprise a preformed hemostatic treatment pad or in the alternative the material may comprise a fluid or powdered medicament. Actuating means are operatively connected to the endoscopic portion for causing a predetermined quantity of the material to be delivered from the endoscopic portion.

In yet another aspect of the present invention, the delivery device is provided with tamping means for manipulating the material delivered.

Further features of the invention will become more apparent from the accompanying drawings and the following detailed description of the invention.

BRIEF DESCRIPTION OF THE DRAWINGS

Preferred embodiments of the invention will be described hereinbelow with reference to the drawings. In the drawings and the description which follows, "proximal" means the end closest to the operator and "distal" means the end farthest from the operator.

FIG. 3 is a perspective view of an alternate embodiment of the handle portion of an endoscopic material delivery device of the subject invention;

FIG. 4 is a perspective view, with parts broken way, of a loaded endoscopic material delivery device;

FIG. 5 is a perspective view of a third embodiment of the handle portion of the endoscopic material delivery device of the subject invention;

FIG. 6 is a perspective view, with portions removed, of a loaded endoscopic material delivery device; and FIG. 7 is a perspective view in partial cutaway of an alternative cartridge means adapted for use in the device of FIG. 6.

DETAILED DESCRIPTION OF THE PREFERRED EMBODIMENTS

Figure 2:
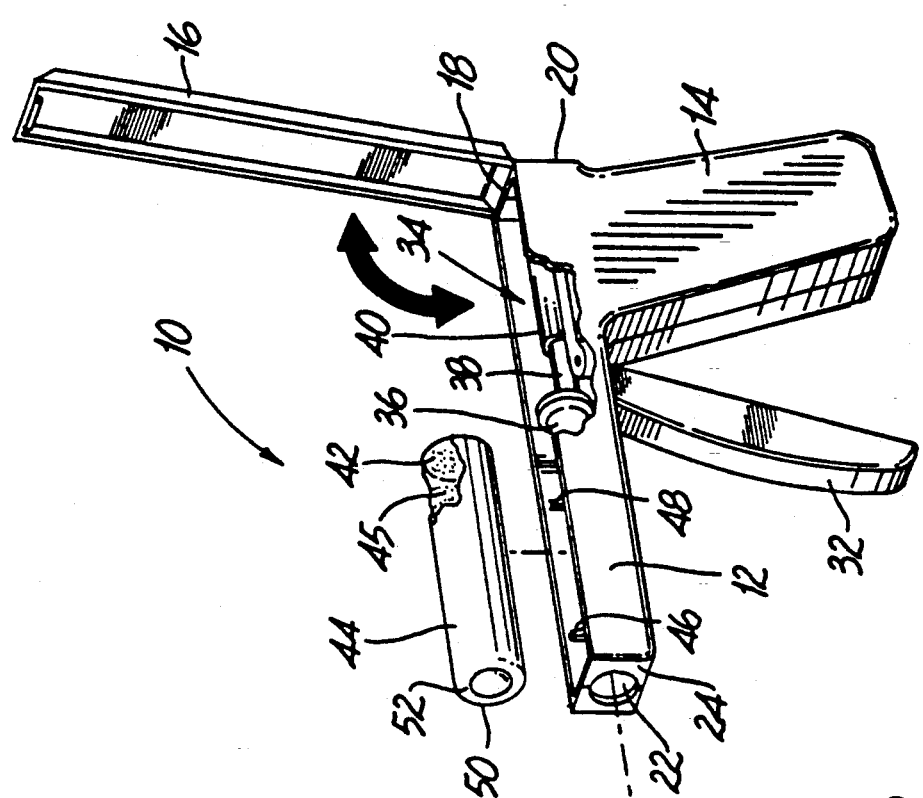
FIG. 2 is a perspective view, with parts broken away, of a loaded endoscopic material delivery device.
Figure 1:
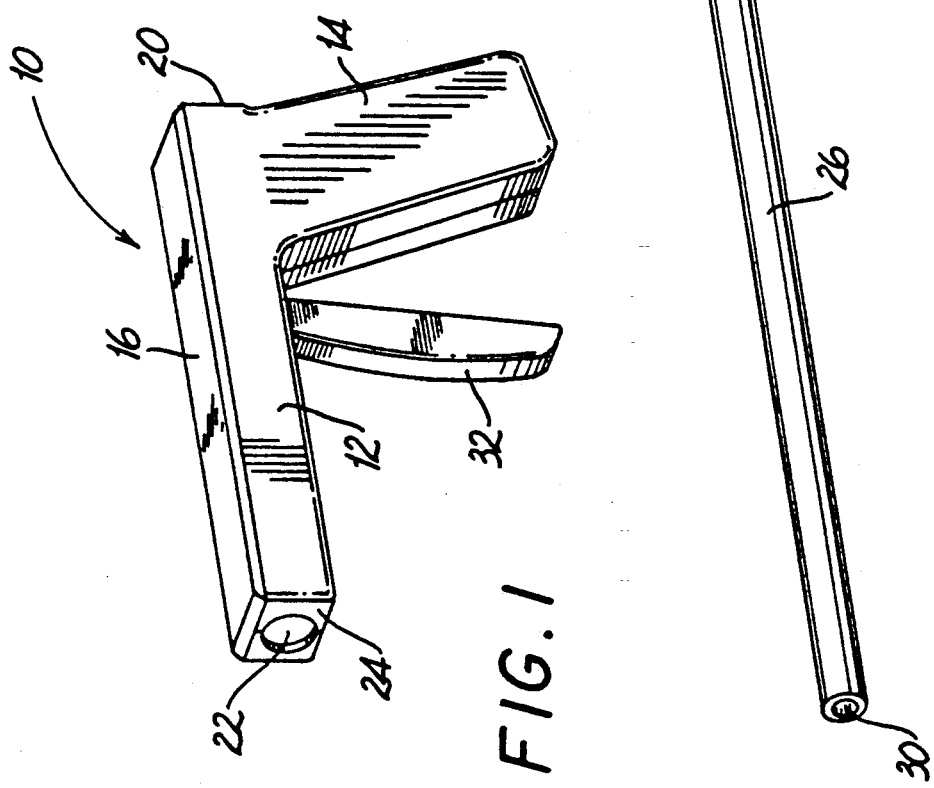
FIG. 1 is a perspective view of the handle portion of an endoscopic material delivery device of the subject invention.

A preferred embodiment of the endoscopic material delivery device of the subject invention is illustrated in FIGS. 1 and 2 and is designated generally by reference numeral 10. The delivery device 10 includes a pistol-like handle portion having a longitudinal barrel portion 12 with a grip portion 14 depending transversely from the barrel portion 12. Portion 14 may be generally rectangular in cross-section as shown or may have any configuration which may be easily and comfortably gripped during operations. Barrel portion 12 includes a cover 16 which is attached thereto by an integral hinge 18 located at the proximal end 20 of the barrel portion 12. A port 22 is formed in the distal end 24 of barrel portion 12 for receiving an elongated disposable endoscopic shaft 26. More particularly, a tapered proximal end 28 of endoscopic shaft 26 may be inserted through the port 22 formed in barrel portion 12 so as to be frictionally or mechanically engaged therein for operations. The endoscopic shaft 26 is formed with an axial passageway 30 through which a metered quantity of material may be delivered to the intended site of application, for example, within the abdominal cavity.

The delivery device 10 further includes a movable trigger 32 which depends transversely from barrel portion 12 adjacent portion 14. In particular, trigger 32 is mechanically linked to a piston mechanism 34 disposed in the barrel portion 12. Piston mechanism 34 includes a circular plunger 36 depending from a shaft 38 which is slidably maintained in a sleeve 40. The trigger 32 is operative to cause shaft 38 to slide within sleeve 40 so that plunger 36 may be moved into contact with the rear end 42 of containment means 44, here shown as a replaceable cylindrical containment cartridge. It should be understood that the containment means 44 may alternatively be a reservoir integrally formed within the barrel 12.

Cartridge 44 which may contain a propellent 45 and/or a powdered or fluid medicament, is maintained in barrel portion 12 on a pair of spaced apart support flanges 46 and 48 disposed adjacent the distal end 24 of barrel portion 12. Furthermore, cartridge 44 may be formed with a penetrable membrane 50 disposed at the front end 52 thereof. The membrane 50 is easily pierced by the tapered end 28 of the endoscopic shaft 26 which extends through the port 22 as the cartridge 44 is urged in a distal direction by the plunger 36.

While described in terms of delivering a medicament, the device of the present invention can be used to deliver a wide variety of fluid, powdered or solid materials. Such materials include, but are not limited to pharmaceuticals, materials having anti-adhesion properties, anti-coagulants, growth factors, osteogenic factors, antibiotics, anti-fungals, immunosuppressive agents, anti-inflammatory agents, irrigating fluids, disinfectants, preservatives, diagnostic agents (dyes, etc.) antihistamines, hormones, enzymes, peptides and/or steroids. Solid materials which may be delivered include woven materials, gels, capsules, molded materials and any other solid form which fits within or may be made to fit within the endoscopic portion of the device.

In operation, a cartridge 44 is placed in support flanges 46 and 48 in the barrel portion 12 of the delivery device 10 and the cover 16 is closed. Thereupon, the endoscopic shaft 26 is inserted into port 22 at end 24 of barrel portion 12. At such a time, the tapered end 28 of endoscopic shaft 26 is disposed proximate the membrane 50 at the front end 52 of cartridge 44. Thereafter, the end 54 of endoscopic shaft 26 is inserted through a cannula (not shown) previously inserted in an incision or entrance wound. When trigger 32 is depressed, the piston mechanism 34 slides forward and plunger 36 is urged against the rear end 42 of cartridge 44 driving the cartridge distally until membrane 50 is pierced by the tapered end 28 of endoscopic portion 26 causing the propellent therein to propel a metered quantity of medicament through the passageway 30 in endoscopic shaft 26 to be delivered into the abdominal cavity.

When cartridge 44 contains a fluid medicament, a first squeeze of the trigger 32 will cause plunger 36 to contact the rear end 42 of cartridge 44. Upon release of the trigger spring means (not shown) urge the trigger back to its original position. Subsequent squeezes of the trigger 32 will move the plunger 36 a predetermined distance into cartridge 44, thus forcing a metered amount of medicament out of cartridge 44 and into the endoscopic portion of the instrument. If the fluid medicament has a high viscosity, a series of squeezes may be required to prime the instrument before the metered amount of medicament is delivered out the distal end of the endoscopic portion.

In a variation of this embodiment, the passageway 30 of endoscopic portion 26 serves as the containment means and is pre-loaded with the medicament to be delivered. Actuating means may directly cause the material to be expelled from the endoscopic portion or, as shown in the figures, the actuating means may act upon container 44 which contains a non-toxic, inert delivery substance which merely acts to force a metered quantity of the medicament out of the endoscopic portion. That is, as plunger 36 advances within cartridge 44, a metered amount of the delivery substance is forced out of cartridge 44 and into endoscopic portion 26, which in turn forces a metered quantity of the medicament out of the distal end of passageway 30. A series of endoscopic portions each loaded with a different medicament may be provided in a kit thus allowing the same handle portion to deliver each medicament as needed without mixing or contamination of the individual medicaments.

Referring to FIGS. 3 and 4, another embodiment of the endoscopic material delivery device of the subject invention is illustrated and is designated generally by reference numeral 60. Delivery device 60 includes a handle portion having a longitudinal barrel portion 62 and a hollow grip portion 64 having a generally circular cross-section projecting transversely from barrel portion 62. A movable trigger 66 depends transversely from barrel portion 62 adjacent portion 64. Barrel portion 64 includes a cover 68 integrally attached at the proximal end 70 thereof and a port 72 formed in the proximal end 74 thereof for receiving the tapered end 28 of an endoscopic shaft 26. As stated previously, the tapered end 28 of the endoscopic shaft 26 is provided for piercing the penetrable membrane 50 at the front end of cartridge 44. The delivery device 60 is further provided with a cap member 76 which is threadably engaged in the bottom 78 of handle portion 64 and which may be readily removed to insert a canister of compressed gas 80.

Trigger 66 is mechanically linked to the canister of compressed gas 85 80 in a known manner known, such as that described in U.S. Pat. No. 4,349,028, the entire disclosure of which is incorporated herein by reference. In addition, a conduit element 82 in barrel portion 62 is connected to the compressed gas canister 80. Conduit element 82 conducts compressed gas from the canister 80 to the rear end 42 of replaceable cartridge 44 which preferably contains a medicament in a powdered form.

In operation, the trigger 66 may be depressed in such a manner as to cause compressed gas to exit canister 80. Thereupon, compressed gas from canister 80 is conducted through conduit element 82 in such a manner as to exert a force upon the rear end 42 of cartridge 44, thereby causing a metered quantity of medicament to be delivered from cartridge 44 through the endoscopic shaft 26 to the intended site of application.

FIGS. 5 and 6 depict another embodiment of the endoscopic material delivery device of the subject invention designated generally by reference numeral 90.

The delivery device 90 includes a longitudinal barrel portion 92 having a proximal end 94, a distal end 96 and a substantially circular midsection 98. A grip portion 100 and a trigger 102 project transversely from barrel portion 92. Barrel portion 92 is provided with a cover member 104 and a threaded port 106 formed in the proximal end 94 thereof. A four bar linkage 108 is operatively disposed in the circular midsection 98 of barrel portion 92. Linkage 108 includes a generally U-shaped key 110 arranged adjacent the proximal end 94 of barrel portion 92. Linkage 108 is operably connected to trigger 102 which when depressed causes linkage 108 to compress in such a manner that the U-shaped key 110 advances distally in barrel portion 92.

An endoscopic member 112 is threadably engageable in port 106 formed in the barrel portion 92. Endoscopic member 112 comprises an elongated tube portion 114 having an axial passageway 116 in which is disposed plunger member 118. A pre-formed treatment pad 120 or a reservoir of medicament is located in the tube 114 distal to the plunger member 118. More particularly, plunger member 118 includes a shaft portion 122 having a circular portion 124 at the proximal end thereof disposed internal of the tube portion 114 and a generally U-shaped key 126 formed at the proximal end thereof disposed external of the tube portion 114. Key 126 on plunger member 118 is engageable with key 110 on linkage 108.

In operation, the endoscopic member 112 may be engaged in the threaded port 106 formed in barrel portion 92 in such a manner so that keys 126 and plunger member 118 are interlocked. Thereupon, trigger 102 may be depressed so as to cause the four bar linkage 108 to compress. At such a time, plunger member 118 is caused to advance proximally in the endoscopic member 112 and force the pre-formed treatment pad 120 from the axial passageway 116 to the intended area of treatment within the abdominal cavity. Thereafter, the portion 124 follows the pre-formed treatment pad 120 out of the proximal end of the endoscopic member 112 and protrudes therefrom. The portion 124 may serve as tamping means. Once extended distally from the endoscopic portion the tamping means may then be manipulated to maneuver the pre-formed treatment pad 120 in a desired position or to manipulate any material delivered from the device.

When the tube portion 114 includes a reservoir of medicament rather than a preformed pad, depressing the trigger 102 advances the plunger member 118 distally to urge a metered quantity of the material from the endoscopic member 112 to the intended site of application.

In an alternate embodiment shown in FIG. 7, the tamping portion of the plunger member 118 may be a frusto-conical shaped portion 128 rather than circular portion 124. Alternatively, portion 124 may be formed with an axial aperture through which medicament stored behind the portion 124 may, upon squeezing the trigger 102, be delivered under pressure.

In an alternative embodiment (not shown) tamping means are disposed in a second passageway formed in the endoscopic portion, and actuating means similar to that described above for delivering material, may be used to deploy the tamping means. The tamping means itself may advantageously be fabricated from an elastic material, such as a synthetic or natural rubber or a shape memory alloy, such as for example the alloys described in U.S. Pat. No. 4,665,906 the disclosure of which is incorporated herein by reference. In a particularly useful embodiment the elastic tamping means is disposed in the second passageway in a deformed state and assumes a substantially undeformed state when deployed out of the passageway to facilitate manipulation of the material just delivered.

Although the invention has been described with reference to preferred embodiments it is apparent that several changes may be made without departing from the spirit and scope of the subject invention.

For example, it may be readily appreciated that the endoscopic portion may be formed integrally with the barrel portion of the device. In this instance the entire device may be disposable. Furthermore, the trigger portion may be disposed substantially parallel to the longitudinal axis of the barrel portion for providing a palm-grip arrangement.

In addition, a separate propellant containment means and medicament containment means may be provided rather than having a combined propellant and medicament cartridge element. In this instance, the barrel portion of the device may be provided with means for supporting and/or interconnecting both cartridges.

Furthermore, it may be readily appreciated that the barrel portion of the device may be formed with an integral reservoir within which medicament is stored for delivery. When the medicament is in a powdered form, it may be propelled from the reservoir by a compressed gas supply stored in the handle portion of the device.

What is claimed is:

1. An endoscopic device for delivering a quantity of material comprising:
    a handle portion;
    an elongated endoscopic portion having a proximal end extending from said handle portion and a distal end, said endoscopic portion having a passageway extending therethrough configured to emit material only from said distal end;
    material containment means disposed within said handle portion for storing at least a particulate material to be delivered and a pressurized propellant for propelling said particulate material from said material containment means, said material containment means including seal means communicating with a proximal end of said passageway for permitting the propulsion of said particulate material therefrom; and
    actuation means operably connected to said material containment means for causing said seal means to open and permit a quantity of said particulate material to be propelled from said material containment means, through said passageway, out of said distal end of said endoscopic portion.

2. An endoscopic device as recited in claim 1 wherein said handle portion is dimensioned and configured for housing said actuation means.

3. An endoscopic device as recited in claim 2 wherein port means is formed in said handle portion for operatively receiving said proximal end of said endoscopic portion.

4. An endoscopic device as recited in claim 2 wherein said handle portion comprises a barrel portion defining a longitudinal axis and a grip portion which depends from said barrel portion, said barrel portion configured for housing said material containment means.

5. An endoscopic device as recited in claim 4 wherein said material containment means comprises a cartridge configured for removal from said barrel portion.

6. An endoscopic device as recited in claim 5 wherein said barrel portion further comprises flange means for supporting said removable cartridge.

7. An endoscopic device as recited in claim 5 wherein said cartridge is formed integral with said material containment means.

8. An endoscopic device as recited in claim 5 wherein said material contained within said cartridge is medicament.

9. An endoscopic device as recited in claim 1 wherein said actuation means includes trigger means movably connected to plunger means for urging said plunger means against said material containment means to cause said seal means to permit pressurized propellent to exit therefrom propelling therewith a quantity of particulate material from said material containment means.

10. A device for endoscopic delivery of a material comprising:
   a handle portion;
   an endoscopic delivery portion extending distally from said handle portion and having a passageway extending therethrough;
   material containment means disposed within said handle portion and communicating with said passageway for storing at least a material to be delivered and a pressurized propellant for propelling said material through said endoscopic delivery portion, said material containment means including seal means for permitting the propulsion of said material therefrom; and
   pivotal actuating means operatively connected to said material containment means for causing said seal means to open and permit a quantity of said material to be delivered from said material containment means.

11. A device as in claim 10 wherein said endoscopic delivery means comprises an elongated endoscopic portion having opposed proximal and distal ends.

12. A device as in claim 11 wherein said passageway is an axial passageway extending from said proximal to said distal end of said endoscopic portion.

13. A device as in claim 12 wherein said handle portion defines a barrel section for housing said material containment means, said proximal end of said endoscopic portion being connected to said barrel section.

14. A device as in claim 13 further comprising port means defined in said barrel section for operatively receiving said proximal end of said endoscopic portion.

15. A device as in claim 13 wherein said material containment means comprises a cartridge configured for removal from said barrel section.

16. An endoscopic device for delivering a quantity of material comprising:
   a handle portion;
   an endoscopic portion having opposed proximal and distal ends, said proximal end connected to said handle portion and having a passageway extending therethrough from said proximal end to said distal end thereof;
   material containment means disposed within said handle portion for storing at least a material to be delivered under pressure, said material containment means including seal means in communication with a proximal end of said passageway for permitting the propulsion of said material therefrom;
   a trigger movably connected to said handle portion; and
   a plunger operatively connected to said trigger for urging said plunger distally against said material containment means to cause said seal means to open and permit at least a portion of the material contained therein to be expelled therefrom so as to be delivered out of said distal end of said endoscopic portion.

17. An endoscopic device for delivering a metered quantity of material comprising:
   a handle portion having a longitudinally extending barrel portion and having opposed proximal and distal ends;
   a port formed in said distal end of said barrel portion;
   a trigger movably connected to said handle portion;
   an elongated endoscopic member having a proximal end portion engageable in said port and having a passageway extending from said proximal end portion to a distal end thereof;
   a removable cartridge disposed in said handle portion and communicating with said passageway, said cartridge containing a pressurized propellent and material for delivery through said passageway in said endoscopic member, said cartridge including a frangible seal member for permitting the pressurized propulsion of said material therefrom; and
   plunger means operatively connected to said trigger for urging said cartridge in a distal direction causing said frangible seal member to be pierced and permit a metered quantity of said material to be expelled therefrom and delivered out of said distal end of said endoscopic member.

18. An endoscopic device as in claim 17 further comprising a grip portion depending from said barrel portion and wherein said trigger is movable between a first position spaced from said grip portion and a second position adjacent said grip portion.

* * * * *